(12) United States Patent
Huyghe et al.

(10) Patent No.: US 8,466,322 B2
(45) Date of Patent: Jun. 18, 2013

(54) PROCESS FOR PREPARING TRI-N-PROPYLAMINE (TPA)

(75) Inventors: Kevin Huyghe, Kapellen (BE); Steven Brughmans, Mannheim (DE); Falk Simon, Bensheim (DE); Johann-Peter Melder, Böhl-Iggelheim (DE); Peter Raatz, Ludwigshafen (DE)

(73) Assignee: BASF SE (DE)

( * ) Notice: Subject to any disclaimer, the term of this patent is extended or adjusted under 35 U.S.C. 154(b) by 76 days.

(21) Appl. No.: 13/173,437

(22) Filed: Jun. 30, 2011

(65) Prior Publication Data
US 2012/0004464 A1    Jan. 5, 2012

Related U.S. Application Data

(60) Provisional application No. 61/359,846, filed on Jun. 30, 2010.

(51) Int. Cl.
  *C07C 209/64* (2006.01)
(52) U.S. Cl.
  USPC .................. 564/463; 564/479; 564/480
(58) Field of Classification Search
  USPC ....................................... 564/463
  See application file for complete search history.

(56) References Cited

U.S. PATENT DOCUMENTS

| | | | |
|---|---|---|---|
| 2,574,693 A | 11/1951 | Engel et al. | |
| 4,014,933 A | 3/1977 | Boettger et al. | |
| 4,234,727 A * | 11/1980 | Toussaint et al. | 544/178 |
| 5,002,922 A | 3/1991 | Irgang et al. | |
| 7,053,246 B2 | 5/2006 | Gerlach et al. | |
| 2003/0013873 A1 | 1/2003 | Neumann et al. | |

FOREIGN PATENT DOCUMENTS

| | | |
|---|---|---|
| CA | 2155171 A1 | 2/1996 |
| CN | 1325842 A | 7/2007 |
| DE | 1953263 A1 | 2/1972 |
| EP | 0379939 | 8/1990 |
| EP | 382049 A1 | 8/1990 |
| EP | 696572 A1 | 2/1996 |
| EP | 963975 A1 | 12/1999 |
| EP | 1270543 A1 | 1/2003 |
| EP | 1431273 A1 | 6/2004 |

OTHER PUBLICATIONS

German Language International Search Report—PCT/EP/2011/060755, Jun. 28, 2011.

* cited by examiner

*Primary Examiner* — Brian J Davis
(74) *Attorney, Agent, or Firm* — Novak Druce Connolly Bove + Quigg LLP

(57) ABSTRACT

Process for preparing tri-n-propylamine (TPA), wherein di-n-propylamine (DPA) is reacted in the presence of hydrogen and a copper-comprising heterogeneous catalyst. An integrated process for preparing TPA, which comprises the following operations:

I) reaction of n-propanol with ammonia in a reactor in the presence of an amination catalyst and optionally hydrogen to form a mixture of mono-n-propylamine, DPA and TPA, II) separation of unreacted ammonia, unreacted n-propanol and possibly hydrogen from the reaction product mixture and recirculation of at least the ammonia and propanol to the reactor in I) and also separation of the n-propylamine mixture by distillation and isolation of the TPA, III) reaction of the DPA obtained in the separation by distillation in II) in a reactor in the presence of hydrogen and a copper-comprising heterogeneous catalyst to form TPA and IV) feeding of the reactor output from III) to operation II).

13 Claims, 1 Drawing Sheet

PROCESS FOR PREPARING TRI-N-PROPYLAMINE (TPA)

CROSS-REFERENCE TO RELATED APPLICATIONS

This application claims the benefit of U.S. Provisional Application 61/359,846 filed on Jun. 30, 2010, the contents of which are incorporated herein by reference in its entirety.

FIELD OF THE INVENTION

The invention relates to a process for preparing tri-n-propylamine (TPA).

BACKGROUND

Tri-n-propylamine (TPA) is, inter alia, an important intermediate for the production of dyes, catalysts and corrosion inhibitors and for use in the pharmaceutical and cosmetics industry (cf., for example, BASF Technical Data Sheet, "Tripropylamine").

In the amination of n-propanol by means of ammonia, a product mixture of mono-n-propylamine (MPA), di-n-propylamine (DPA) and tri-n-propylamine (TPA) is always obtained. The composition of the amine product mixture formed can largely be controlled via the process parameters in the reaction of propanol. However, the proportion of di-n-propylamine, in particular, in the product mixture is difficult to influence and it is often impossible to produce exactly the amine product mixture wanted by the market.

One possible way of controlling the amine product mixture would be the separate conversion of dialkylamine into trialkylamine by reaction with n-propanol. However, this possibility is not preferred for process engineering and chemical reasons [risk of runaway reactions (uncontrolled temperature rise), safety aspect].

It is known from NL 65644 and the equivalent U.S. Pat. No. 2,574,693 (Shell Dev. Comp.) that monobutylamine can be converted into dibutylamine over an $Al_2O_3$ catalyst in the presence of ammonia at high temperatures.

CN 1,325,842 A (Chinese Petro. Chem. Group) teaches the conversion of monoisopropylamine into diisopropylamine over a K/H-beta-zeolite at elevated temperature.

BRIEF SUMMARY

It was an object of the present invention to overcome the disadvantages of the prior art and provide an improved economical process for preparing tri-n-propylamine (TPA). The production process should give tri-n-propylamine in high yield, space-time yield (STY) and selectivity and also be particularly simple and economical.

It was recognized according to the invention that the di-n-propylamine formed, for example, by prior amination of n-propanol can be converted into tri-n-propylamine by a reaction (scrambling) of di-n-propylamine, optionally in the presence of ammonia, preferably in the absence of ammonia, and the n-propylamine product mix of a preceding n-propylamine synthesis can therefore be altered in a targeted manner in favor of the tertiary amine.

We have accordingly found a process for preparing tri-n-propylamine, in which di-n-propylamine is reacted in the presence of hydrogen and a copper-comprising heterogeneous catalyst. The reaction of DPA proceeds according to the scheme

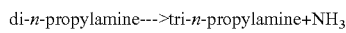

di-*n*-propylamine--->tri-*n*-propylamine+$NH_3$

Small amounts of mono-n-propylamine are obtained as by-product.

In the disproportionation, di-n-propylamine is reacted over a copper-comprising heterogeneous catalyst. Preferably elevated pressure, preferably elevated temperature and the presence of hydrogen are the typical reaction conditions.

The reaction is preferably carried out an absolute pressure in the range from 20 to 150 bar, in particular from 40 to 150 bar, more particularly from 60 to 150 bar.

The reaction is preferably carried out at a temperature in the range from 180 to 260° C., in particular from 190 to 260° C., more particularly from 200 to 260° C.

The space velocity over the catalyst is preferably in the range from 0.3 to 3 kg/l·h, in particular from 0.3 to 0.7 kg/l·h, more particularly from 0.4 to 0.7 kg/l·h [kg of DPA/(liters of catalyst·hour)].

(Liters of catalyst=catalyst bed volume)

The amount of hydrogen used is preferably in the range from 200 to 2000 standard l/l·h, in particular from 250 to 700 standard l/l·h, more particularly from 300 to 600 standard l/l·h [standard liters (liters of catalyst·hour)]

(standard l=standard liters=volume under standard conditions (20° C., 1 bar absolute).

The process can be carried out continuously or batchwise. Preference is given to a continuous process.

BRIEF DESCRIPTION OF THE DRAWINGS

Illustrative embodiments of the present invention are described herein with reference to the accompanying drawings, in which.

DETAILED DESCRIPTION OF THE PREFERRED EMBODIMENTS

Figure 1:
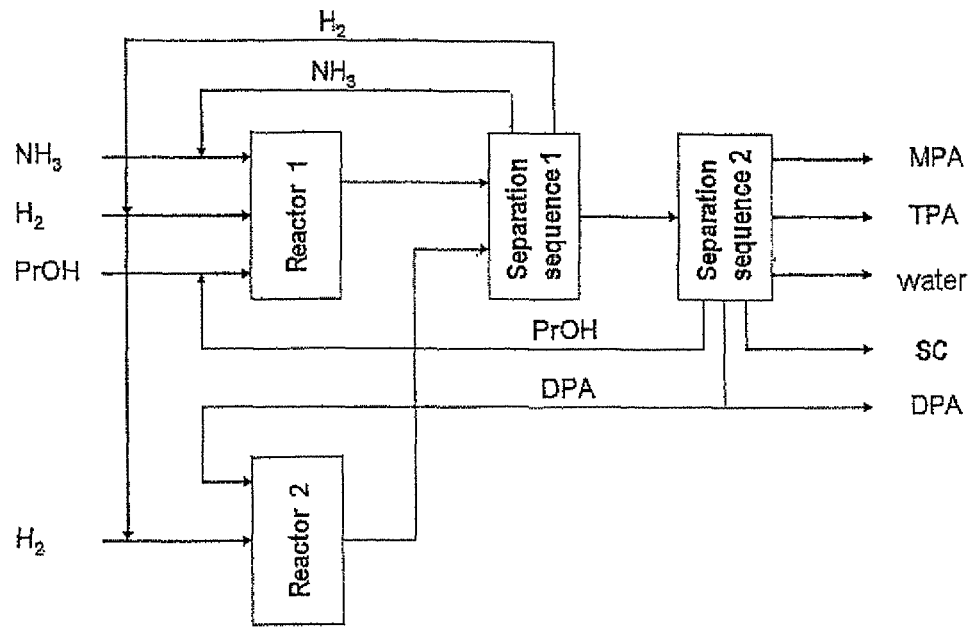
FIG. 1 is a schematic diagram depicting one embodiment of the integrated process for preparing tri-n-propylamine (TPA).

For the synthesis, the starting material (DPA) is preferably heated in a stream of hydrogen and fed into the reactor. Hydrogen is preferably circulated in a gas recycle mode.

The starting material (DPA) can optionally be recirculated from a distillation column in which the reaction product mixture has been fractionated.

The starting material (DPA) can also be heated as an aqueous solution and passed to the catalyst bed, preferably with the gas recycle stream.

Preferred reactors are tube reactors. Examples of suitable reactors having a gas recycle stream may be found in Ullmann's Encyclopedia of Industrial Chemistry, 5th Ed., vol. B 4, pages 199-238, "Fixed-Bed Reactors".

As an alternative, the reaction is advantageously carried out in a shell-and-tube reactor or in a monostream plant.

In a monostream plant, the tube reactor in which the reaction is carried out can comprise a plurality of, (e.g. two or three) individual tube reactors connected in series. Optionally, intermediate introduction of feed (comprising the starting material DPA and/or $H_2$) and/or recycle gas and/or reactor output from a downstream reactor is advantageously possible here.

The heterogeneous catalyst used in the process of the invention comprises Cu and/or Ni and/or Co, preferably Cu and Ni and/or Co, particularly preferably Cu and Ni and Co.

The heterogeneous catalyst preferably comprises an oxidic support material for the active metals, preferably aluminum oxide (gamma, delta, theta, alpha, kappa, chi or mixtures thereof) and/or zirconium dioxide (preferably monoclinic, tetragonal or cubic modification). A particularly preferred support material is aluminum oxide, in particular gamma-aluminum oxide.

In the process of the invention, the catalysts are preferably used in the form of catalysts which consist only of catalytically active composition and optionally a shaping aid (e.g. graphite or stearic acid) if the catalyst is used as shaped bodies, i.e. do not comprise further catalytically active constituents.

In this context, the oxidic support material aluminum oxide ($Al_2O_3$), zirconium dioxide ($ZrO_2$) are considered to be part of the catalytically active composition.

The catalysts are used by introducing the catalytically active composition which has been milled to powder into the reaction vessel or by milling the catalytically active composition, mixing it with shaping aids, shaping and heat treatment to give shaped catalyst bodies, for example pellets, spheres, rings, extrudates (e.g. rods), and arranging the shaped catalyst bodies in the reactor.

The concentrations indicated (in % by weight) for the components of the catalyst are in each case, unless indicated otherwise, based on the catalytically active composition of the finished catalyst after its last heat treatment and before reduction with hydrogen.

The catalytically active mass of the catalyst after its last heat treatment and before reduction with hydrogen is defined as the sum of the masses of the catalytically active constituents and the abovementioned catalyst support materials and comprises essentially the following constituents:
aluminum oxide ($Al_2O_3$) and/or zirconium dioxide ($ZrO_2$) and oxygen-comprising compounds of copper and/or of nickel and/or of cobalt.

The sum of the abovementioned constituents of the catalytically active composition is usually from 70 to 100% by weight, preferably from 80 to 100% by weight, particularly preferably from 90 to 100% by weight, in particular >95% by weight, very particularly >98% by weight, more particularly >99% by weight, e.g. particularly preferably 100% by weight.

The catalytically active composition of the catalysts according to the invention and catalysts used in the process of the invention can further comprise one or more elements (oxidation state 0) or inorganic or organic compounds thereof selected from groups I A to VI A and I B to VII B and VIII of the Periodic Table.

Examples of such elements and compounds thereof are:
transition metals such as Mn and $MnO_2$, Mo and $MoO_3$, W and tungsten oxides, Ta and tantalum oxides, Nb and niobium oxides or niobium oxalate, V and vanadium oxides and vanadyl pyrophosphate; lanthanides such as Ce and $CeO_2$ or Pr and $Pr_2O_3$; alkaline earth metal oxides such as SrO; alkaline earth metal carbonates such as $MgCO_3$, $CaCO_3$ and $BaCO_3$; alkali metal oxides such as $Na_2O$, $K_2O$; alkali metal carbonates such as $Li_2CO_3$, $Na_2CO_3$ and $K_2CO_3$; boron oxide ($B_2O_3$).

The catalytically active composition of the catalyst used in the process of the invention preferably comprises no rhenium, no ruthenium, no iron and/or no zinc, in each case neither in metallic (oxidation state=0) form nor in an ionic (oxidation state≠0), in particular oxidized, form.

The catalytically active composition of the catalyst used in the process of the invention preferably comprises no silver and/or molybdenum, in each case neither in metallic (oxidation state=0) form nor in an ionic (oxidation state≠0), in particular oxidized, form.

The catalytically active composition of the catalyst preferably comprises no oxygen-comprising compounds of silicon and/or of chromium.

The catalysts can be produced by known methods, e.g. by precipitation, precipitation onto a support, impregnation.

The catalytically active composition of preferred heterogeneous catalysts before treatment with hydrogen comprises
from 20 to 85% by weight, preferably from 20 to 65% by weight, particularly preferably from 22 to 40% by weight, of oxygen-comprising compounds of zirconium, calculated as $ZrO_2$,
from 1 to 30% by weight, particularly preferably from 2 to 25% by weight, of oxygen-comprising compounds of copper, calculated as CuO,
from 14 to 70% by weight, preferably from 15 to 50% by weight, particularly preferably from 21 to 45% by weight, of oxygen-comprising compounds of nickel, calculated as NiO, with the molar ratio of nickel to copper, preferably being greater than 1, in particular greater than 1.2, very particularly preferably from 1.8 to 85, and
from 0 to 5% by weight, in particular from 0.1 to 3% by weight, of oxygen-comprising compounds of molybdenum, calculated as $MoO_3$.

In a further variant, the catalytically active composition of these preferred catalysts before treatment with hydrogen additionally comprises
from 15 to 50% by weight, particularly preferably from 21 to 45% by weight, of oxygen-comprising compounds of cobalt, calculated as CoO.

The oxygen-comprising compounds of copper, nickel and optionally cobalt, in each case calculated as CuO, NiO and CoO, of the preferred catalysts are generally comprised in total amounts of from 15 to 80% by weight, preferably from 35 to 80% by weight, particularly preferably from 60 to 78% by weight, in the catalytically active composition (before treatment with hydrogen), with the molar ratio of nickel to copper particularly preferably being greater than 1.

The catalytically active composition of particularly preferred heterogeneous catalysts before treatment with hydrogen comprises
from 20 to 90% by weight, preferably from 40 to 85% by weight, particularly preferably from 60 to 80% by weight, of oxygen-comprising compounds of aluminum, calculated as $Al_2O_3$,
from 1 to 30% by weight, preferably from 2 to 25% by weight, particularly preferably from 3 to 20% by weight, of oxygen-comprising compounds of copper, calculated as CuO,
from 1 to 40% by weight, preferably from 3 to 30% by weight, particularly preferably from 5 to 20% by weight, of oxygen-comprising compounds of nickel, calculated as NiO, with the molar ratio of nickel to copper particularly preferably being greater than 1, preferably greater than 1.2, particularly preferably from 1.8 to 8.5, and
from 1 to 40% by weight, preferably from 3 to 30% by weight, particularly preferably from 5 to 20% by weight, of oxygen-comprising compounds of cobalt, calculated as CoO.

The oxygen-comprising compounds of nickel, cobalt and copper, in each case calculated as NiO, CoO and CuO, are preferably comprised in total amounts of from 10 to 80% by weight, particularly preferably from 15 to 60% by weight, very particularly preferably from 20 to 40% by weight, in the catalytically active composition (before treatment with hydrogen), with the molar ratio of nickel to copper particularly preferably being greater than 1.

Further preferred heterogeneous catalysts in the process of the invention are catalysts which are disclosed in DE 19 53 263 A (BASF AG) and comprise cobalt, nickel and copper and aluminum oxide and/or silicon dioxide and have a metal content of from 5 to 80% by weight, in particular from 10 to 30% by weight, based on the total catalyst, where the catalysts comprise, calculated on the basis of the metal content, from 70 to 95% by weight of a mixture of cobalt and nickel and from 5 to 30% by weight of copper and the weight ratio of cobalt to nickel is from 4:1 to 1:4, in particular from 2:1 to 1:2, for example the catalyst having the composition 10% by weight of CoO, 10% by weight of NiO and 4% by weight of CuO on $Al_2O_3$ used in the examples there, catalysts which are disclosed in EP 382 049 A (BASF AG) or catalysts which can be produced correspondingly and whose catalytically active composition before treatment with hydrogen comprises from 20 to 85% by weight, preferably from 70 to 80% by weight, of $ZrO_2$ and/or $Al_2O_3$, from 1 to 30% by weight, preferably from 1 to 10% by weight, of CuO, and from 1 to 40% by weight, preferably from 5 to 20% by weight, of each of CoO and NiO, for example the catalysts described in loc. cit. on page 6 which have the composition 76% by weight of Zr, calculated as ZrO2, 4% by weight of Cu, calculated as CuO, 10% by weight of Co, calculated as CoO, and 10% by weight of Ni, calculated as NiO, catalysts which are disclosed in EP 963 975 A (BASF AG) and whose catalytically active composition before treatment with hydrogen comprises from 22 to 40% by weight of $ZrO_2$, from 1 to 30% by weight of oxygen-comprising compounds of copper, calculated as CuO, from 15 to 50% by weight of oxygen-comprising compounds of nickel, calculated as NiO, with the molar ratio of Ni:Cu being greater than 1, from 15 to 50% by weight of oxygen-comprising compounds of cobalt, calculated as CoO, from 0 to 10% by weight of oxygen-comprising compounds of aluminum and/or manganese, calculated as $Al_2O_3$ or $MnO_2$, and no oxygen-comprising compounds of molybdenum, for example the catalyst A which is disclosed in loc. cit., page 17, and has the composition 33% by weight of Zr, calculated as ZrO2, 28% by weight of Ni, calculated as NiO, 11% by weight of Cu, calculated as CuO, and 28% by weight of Co, calculated as CoO, catalysts which are disclosed in EP 696 572 A (BASF AG) and whose catalytically active composition before reduction with hydrogen comprises from 20 to 85% by weight of $ZrO_2$, from 1 to 30% by weight of oxygen-comprising compounds of copper, calculated as CuO, from 30 to 70% by weight of oxygen-comprising compounds of nickel, calculated as NiO, from 0.1 to 5% by weight of oxygen-comprising compounds of molybdenum, calculated as $MoO_3$, and from 0 to 10% by weight of oxygen-comprising compounds of aluminum and/or manganese, calculated as $Al_2O_3$ or $MnO_2$, for example the catalyst which is disclosed in loc. cit., page 8, and has the composition 31.5% by weight of $ZrO_2$, 50% by weight of NiO, 17% by weight of CuO and 1.5% by weight of $MoO_3$, catalysts which are described in EP 1 270 543 A1 (BASF AG) and comprise at least one element or compound of an element of groups VIII and IB of the Periodic Table, and catalysts which are described in EP 1 431 273 A (BASF AG) and in the production of which a precipitation of catalytically active components onto monoclinic, tetragonal or cubic zirconium dioxide has been carried out.

The catalysts produced can be stored as such. Before use as catalysts in the process of the invention, they are prereduced by treatment with hydrogen (=activation of the catalyst). However, they can also be used without prereduction, in which case they are then reduced (=activated) by the hydrogen present in the reactor under the conditions of the process of the invention.

To activate the catalyst, it is preferably exposed to a hydrogen-comprising atmosphere or a hydrogen atmosphere at a temperature in the range from 100 to 500° C., in particular from 150 to 400° C., very particularly preferably from 180 to 300° C., for a period of at least 25 minutes, in particular at least 60 minutes. The time for which the catalyst is activated can be up to 1 h, particularly preferably up to 12 h, in particular up to 24 h.

During this activation, at least part of the oxygen-comprising metal compounds present in the catalysts is reduced to the corresponding metals, so that these are present together with the various oxygen compounds in the active form of the catalyst.

According to the invention, the process of the invention is, in particular, carried out for preparing TPA by the above-described disproportionation of di-n-propylamine in an integrated process in which tri-n-propylamine (TPA), in particular, is prepared selectively as described below. The integrated process allows precise control of the proportions in the amine product mixture of mono-n-propylamine (MPA), di-n-propylamine (DPA) and tri-n-propylamine (TPA). This high product flexibility advantageously enables the product mix wanted by the market to be prepared precisely.

Figure 2:
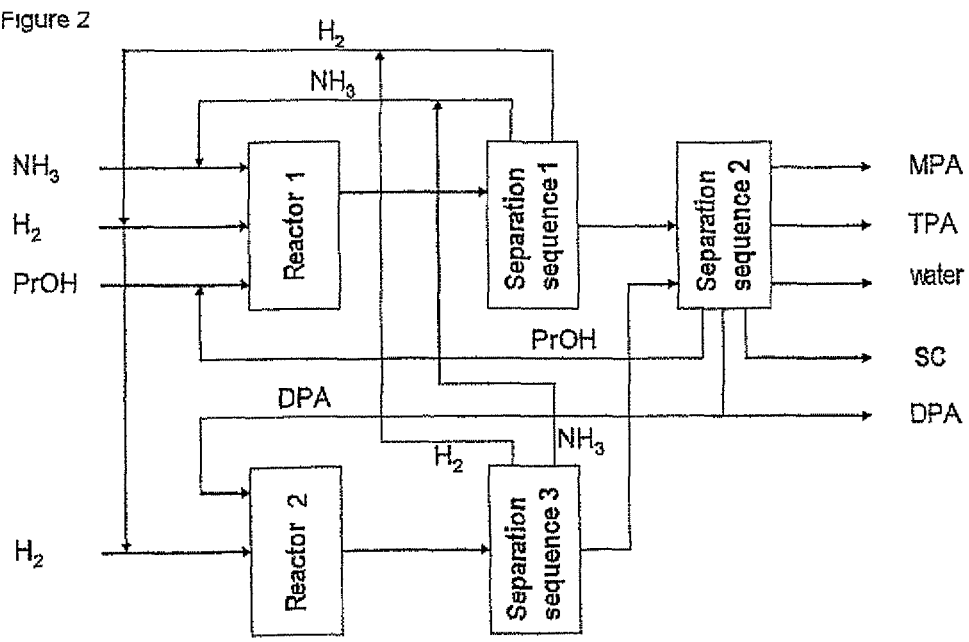
FIG. 2 is a schematic diagram depicting another embodiment of the integrated process for preparing tri-n-propylamine (TPA).

See FIGS. 1 and 2 for preferred embodiments.

An amination of n-propanol takes place, preferably continuously, in a main reactor. For this purpose, n-propanol (PrOH) is reacted with ammonia over an amination catalyst and optionally in the presence of hydrogen to give a mixture of mono-n-propylamine, di-n-propylamine and tri-n-propylamine. The reaction of n-propanol with ammonia in the main reactor (reactor 1), which can naturally also be divided into two or more reactors connected in series or in parallel, can be carried out by processes known to those skilled in the art (see, for example, Kirk-Othmer Encyclopedia of Chemical Technology, vol. 2, pages 537-553).

Ammonia, n-propanol and optionally hydrogen are separated off from the reaction product mixture and of these at least ammonia and propanol are recirculated to the reactor. In addition, mono-n-propylamine, di-n-propylamine and tri-n-propylamine are separated by distillation, e.g. in a cascade of distillation columns.

Di-n-propylamine which has been separated off is fed into a reactor (converting reactor) in which, according to the invention, the reaction to form TPA occurs, preferably continuously, in the presence of a copper-comprising heterogeneous catalyst.

The output from the converting reactor is fed to the above-mentioned work-up section for the reaction product mixture from the main reactor.

Such an integrated mode of operation allows tri-n-propylamine to be prepared from n-propanol with high selectivity, e.g. in the range from 40 to 99% (based on n-propanol).

Particular and preferred embodiments of the process are as follows:

The reaction of n-propanol with ammonia is carried out in a reactor (reactor 1), preferably over a transition metal catalyst, e.g. a copper- and/or nickel-comprising catalyst, at generally from 1 to 220 bar and generally from 130 to 250° C., or over an acid catalyst, e.g. a metal oxide or zeolite at generally from 1 to 36 bar and generally from 300 to 500° C.

The catalyst is preferably arranged as a fixed bed in the reactor (reactor 1).

The propanol conversion is generally maintained at >90%, preferably >95%.

To maintain the catalyst activity, hydrogen is preferably also fed into the reactor (reactor 1) when metal catalysts are used.

The output from the reactor for the n-propanol reaction (reactor 1) is subsequently depressurized to preferably from 20 to 30 bar. Any "low-pressure hydrogen" obtained, which may still comprise some ammonia, can be compressed and circulated via the reactor for the n-propanol reaction (reactor 1) and/or can, optionally after compression, be used directly (or after removal of ammonia comprised therein by means of a gas scrub) as feed for the reactor for the DPA reaction (reactor 2) (see below).

The reaction product mixture remaining after the hydrogen has been separated off, which comprises essentially or consists of ammonia, water, n-propanol, MPA, DPA and TPA, is separated into the individual constituents according to the different vapor pressures. The multistage separation into the constituents is preferably carried by distillation, in particular by continuous distillation, and/or by liquid-liquid phase separation, in particular by continuous liquid-liquid phase separation. Such separation processes are known to those skilled in the art, e.g. from Kirk-Othmer Encyclopedia of Chemical Technology.

The distillation columns required for obtaining the individual products, especially the desired propylamines, in pure form by distillation can be designed by a person skilled in the art using familiar methods (e.g. number of theoretical plates, reflux ratio, etc.).

The separation of the reaction product mixture resulting from the reactor for the n-propanol reaction (reactor 1) is particularly preferably carried out in two separation sequences by multistage distillation, with ammonia and any hydrogen present firstly being separated off in the first separation sequence (separation sequence 1) and a separation into n-propanol, MPA, DPA, TPA, water and secondary components (SC) being carried out in the second separation sequence (separation sequence 2).

Any n-propanol obtained as a result of incomplete reaction in this separation of the reaction product mixture resulting from the reactor for the n-propanol reaction (reactor 1) is preferably recirculated to the reactor (reactor 1).

The dipropylamine (DPA) obtained in this separation is, optionally after branching off a partial amount into a storage tank, fed into a separate reactor (converting reactor, reactor 2) for conversion into tri-n-propylamine (TPA) in the presence of a copper-comprising heterogeneous catalyst.

The disproportionation of DPA to form TPA in the separate reactor (reactor 2), which can naturally also be divided into two or more reactors connected in series or in parallel, is carried out according to the above-described process.

To maintain the catalyst activity, hydrogen is fed into the reactor (reactor 2).

The ammonia- and hydrogen-comprising reaction product mixture from the separate conversion of DPA into TPA is, in an embodiment of the integrated process of the invention (variant 1), combined with the output from the reactor for the n-propanol reaction (reactor 1) and the two are worked up together, i.e. fed to the separation of the reaction product mixture resulting from the reactor for the n-propanol reaction (reactor 1), in particular to the first separation sequence (separation sequence 1) of the separation of the reaction product mixture resulting from the reactor for the n-propanol reaction (reactor 1).

A process scheme of this variant 1 of the integrated process of the invention is shown in the appendix (FIG. 1).

In a further embodiment of the integrated process of the invention (variant 2), hydrogen and ammonia are firstly separated off (separation sequence 3) from the reaction product mixture from the separate conversion of DPA into TPA and are preferably each recirculated (ammonia to the reactor for the n-propanol reaction (reactor 1), hydrogen to the reactor for the n-propanol reactor (reactor 1) and/or the reactor for the DPA reaction (reactor 2)) and the remaining reaction product mixture comprising n-propylamines is then fed to the second separation sequence (separation sequence 2) of the separation of the reaction product mixture resulting from the reactor for the n-propanol reaction (reactor 1).

A process scheme of this variant 2 of the integrated process of the invention is shown in the appendix (FIG. 2).

The integration of the disproportionation stage into a conventional n-propylamine production process based on n-propanol enables the outputs from the two reactions to be advantageously worked up together.

Liberated ammonia obtained in the work-up can be recirculated to the amination of n-propanol (reactor 1) and hydrogen obtained in the work-up can be recirculated to the converting reactor (reactor 2) and/or to the amination of n-propanol (reactor 1).

All pressures indicated are absolute pressures.

EXAMPLES

Catalyst "A S4"

The catalyst "A S4", a Cu/Co/Ni/gamma-$Al_2O_3$ catalyst as disclosed in DE 19 53 263 A (BASF AG), was produced by impregnation of 4 mm extrudates.

The catalyst had the following composition before treatment (activation) with hydrogen:
10% by weight of CoO, 10% by weight of NiO and 4% by weight of CuO on gamma-$Al_2O_3$.

Example 1

The starting material 100% DPA was disproportionated continuously in the absence of $NH_3$ over the catalyst "A S4". At a pressure of 140 bar, a space velocity of 0.50 kg/l·h and an amount of hydrogen of 500 standard l/l·h, the following composition of the reaction product mixture (in % by weight) was obtained at 250° C.: 4% of MPA, 51% of DPA and 45% of TPA.

Example 2

The starting material 100% DPA was disproportionated continuously in the absence of $NH_3$ over the catalyst "A S4". At a pressure of 85 bar, a space velocity of 0.51 kg/l·h and an amount of hydrogen of 400 standard l/l·h, the following composition of the reaction product mixture (in % by weight) was obtained at 220° C.: 4% of MPA, 47% of DPA and 49% of TPA.

Example 3

The starting material 100% DPA was disproportionated continuously in the absence of $NH_3$ over the catalyst "A S4". At a pressure of 40 bar, a space velocity of 0.59 kg/l·h and an amount of hydrogen of 405 standard l/l·h, the following composition of the reaction product mixture (in % by weight) was obtained at 215° C.: 5% of MPA, 50% of DPA and 45% of TPA.

Example 4

The starting material 100% DPA was disproportionated continuously in the absence of $NH_3$ over the catalyst "A S4". At a pressure of 140 bar, a space velocity of 0.50 kg/l·h and an amount of hydrogen of 600 standard l/l·h, the following composition of the reaction product mixture (in % by weight) was obtained at 250° C.: 4% of MPA, 50% of DPA and 46% of TPA.

Example 5

The starting material 100% DPA was disproportionated continuously in the absence of $NH_3$ over the catalyst "A S4". At a pressure of 40 bar, a space velocity of 3.00 kg/l·h and an amount of hydrogen of 200 standard l/l·h, the following composition of the reaction product mixture (in % by weight) was obtained at 240° C.: 6% of MPA, 51% of DPA and 43% of TPA.

Example 6

The starting material 100% DPA was disproportionated continuously in the absence of $NH_3$ over the catalyst "A S4". At a pressure of 85 bar, a space velocity of 0.50 kg/l·h and an amount of hydrogen of 200 standard l/l·h, the following composition of the reaction product mixture (in % by weight) was obtained at 200° C.: 4% of MPA, 57% of DPA and 39% of TPA.

The invention claimed is:

1. A process for preparing tri-n-propylamine comprising reacting di-n-propylamine in the presence of hydrogen and a copper-comprising heterogeneous catalyst.

2. The process according to claim 1, wherein di-n-propylamine is reacted in the presence of a copper and nickel-comprising heterogeneous catalyst.

3. The process according to claim 1, wherein di-n-propylamine is reacted in the presence of a copper and nickel and cobalt-comprising heterogeneous catalyst.

4. The process according to claim 1, wherein the heterogeneous catalyst comprises aluminum oxide and/or zirconium dioxide as support material.

5. The process according to claim 1, wherein no ammonia ($NH_3$) is used.

6. The process according to claim 1, wherein the catalytically active composition of the heterogeneous catalyst before treatment with hydrogen comprises:
   from 20 to 90% by weight of oxygen-comprising compounds of aluminum, calculated as $Al_2O_3$,
   from 1 to 30% by weight of oxygen-comprising compounds of copper, calculated as CuO,
   from 3 to 30% by weight of oxygen-comprising compounds of nickel, calculated as NiO, and
   from 3 to 30% by weight of oxygen-comprising compounds of cobalt, calculated as CoO.

7. The process according to claim 1, wherein the reaction is carried out at an absolute pressure in the range from 20 to 150 bar.

8. The process according to claim 1, wherein the reaction is carried out at a temperature in the range from 180 to 260° C.

9. The process according to claim 1, wherein the reaction is carried out continuously.

10. The process according to claim 1, wherein the reaction is carried out at a space velocity over the catalyst in the range from 0.3 to 3 kg of di-n-propylamine/(liters of catalyst·hour).

11. The process according to claim 1, wherein the amount of hydrogen used is in the range from 200 to 2000 standard liters/(liters of catalyst·hour).

12. An integrated process for preparing tri-n-propylamine (TPA) comprising:
   I) reacting n-propanol with ammonia in a reactor in the presence of an amination catalyst and optionally hydrogen to form a mixture of mono-n-propylamine, di-n-propylamine (DPA) and TPA,
   II) separating unreacted ammonia, unreacted n propanol and possibly hydrogen from the reaction product mixture and recirculating at least the ammonia and propanol to the reactor in I) and also separating the n-propylamine mixture by distillation and isolation of the TPA,
   III) reacting the DPA obtained in the separation by distillation in II) in a reactor by a process according to claim 1 to form TPA and
   IV) feeding of the reactor output from III) to operation II).

13. The integrated process according to claim 12, wherein the ammonia formed in III) and hydrogen are first separated off from the reactor output from III) before operation IV) and at least the ammonia is recirculated to the reactor in I).

* * * * *